US007579316B2

(12) United States Patent
Khare et al.

(10) Patent No.: US 7,579,316 B2
(45) Date of Patent: Aug. 25, 2009

(54) COMPOSITIONS AND METHODS TO MODULATE AN IMMUNE RESPONSE TO AN IMMUNOGENIC THERAPEUTIC AGENT

(75) Inventors: Sanjay D. Khare, Newbury Park, CA (US); Ulrich Feige, Benglen (CH)

(73) Assignee: Amgen Inc., Thousand Oaks, CA (US)

( * ) Notice: Subject to any disclaimer, the term of this patent is extended or adjusted under 35 U.S.C. 154(b) by 375 days.

(21) Appl. No.: 11/057,923

(22) Filed: Feb. 14, 2005

(65) Prior Publication Data

US 2005/0287152 A1   Dec. 29, 2005

Related U.S. Application Data

(63) Continuation of application No. PCT/US2004/035415, filed on Oct. 26, 2004.

(60) Provisional application No. 60/515,199, filed on Oct. 27, 2003.

(51) Int. Cl.
*A61K 38/16* (2006.01)
*A61K 38/17* (2006.01)
*C07K 14/705* (2006.01)
*C07K 16/46* (2006.01)

(52) U.S. Cl. .................. 514/12; 514/21; 424/134.1; 530/350; 530/387.3

(58) Field of Classification Search .................. None
See application file for complete search history.

(56) References Cited

U.S. PATENT DOCUMENTS

| | | | |
|---|---|---|---|
| 3,773,919 | A | 11/1973 | Boswell |
| 4,289,872 | A | 9/1981 | Denkewalter et al. |
| 4,710,473 | A | 12/1987 | Morris |
| 5,229,490 | A | 7/1993 | Tam |
| 6,251,957 | B1 * | 6/2001 | Wilson et al. ............. 424/85.2 |
| 6,372,208 | B1 | 4/2002 | Wilson et al. |
| 6,444,792 | B1 * | 9/2002 | Gray et al. ................ 530/387.3 |
| 2003/0211078 | A1 * | 11/2003 | Heavner ..................... 424/85.1 |

FOREIGN PATENT DOCUMENTS

| | | |
|---|---|---|
| EP | 036676 | 9/1981 |
| EP | 058481 | 8/1982 |
| EP | 088046 | 9/1983 |
| EP | 133988 | 3/1985 |
| EP | 143949 | 6/1985 |
| EP | 0422339 | 4/1991 |
| WO | WO 92/16221 | 10/1992 |
| WO | WO 93/21259 | 10/1993 |
| WO | WO 95/34326 | 12/1995 |
| WO | WO 96/32478 | 10/1996 |
| WO | WO 97/34631 | 9/1997 |
| WO | WO 98/33513 | 8/1998 |
| WO | WO 00/24782 | 5/2000 |
| WO | WO 01/92337 | 12/2001 |
| WO | WO 02/02638 | 1/2002 |

OTHER PUBLICATIONS

Levi-Montalcini et al., *J. Neurol. Sci.*, 1995, 130: 119-127.*
Cohen et al., 1986, Press Release of the Nobel Assembly at the Karolinska Institute, 5 pages.*
Chamberlain, P. et al. "An Overview of Scientific and Regulatory Issues for the Immunogenicity of Biological Products." *Immunogenicity of Therapeutic Biological Products, Dev. Biol. Basel, Karger* 112:3-11 (2003).
Chang, C-C.J. et al. "Evolution of a Cytokine Using DNA Family Shuffling." *Nature Biotechnology* 17:793-797 (1999).
Davis, C.G. et al. "Transgenic Mice as a Source of Fully Human Antibodies for the Treatment of Cancer." *Cancer and Metastasis Reviews* 18:421-425 (1999).
Ellison, J.W. et al. "The Nucleotide Sequence of a Human Immunoglobulin $C\gamma_1$ Gene." *Nucleic Acids Res.* 10: 4071-79 (1982).
Eppstein, D.A. et al. "Biological Activity of Liposome-Encapsulated Murine Interferon $\gamma$ is Mediated by a Cell Membrane Receptor." *Proc. Natl. Acad. Sci. USA* 82:3688-3692 (1985).
Green, L.L. "Antibody Engineering Via Genetic Engineering of the Mouse: ZenoMouse Strains are a Vehicle for the Facile Generation of Therapeutic Human Monoclonal Antibodies." *J. Immunol. Meth.* 231:11-23 (1999).
Herzyk, D.J. "The Immunogenicity of Therapeutic Cytokines." *Current Opinion in Molecular Therapeutics* 5(2):167-171 (2003).
Isaacs, J.D. "The Antiglobulin Response to Therapeutic Antibodies." *Seminars in Immunology* 2(6):449-456 (1990).
Issacs, J.D. "From Bench to Bedside: Discovering Rules for Antibody Design, and Improving Serotherapy with Monoclonal Antibodies." *Rheumatology* 40:724-738 (2001).
Koren, E. et al. "Immune Responses to Therapeutic Proteins in Humans—Clinical Significance, Assessment and Prediction." *Current Pharmaceutical Biotechnology* 3(4):349-360 (2002).
Kurtzman, A.L. et al. "Advances in Directed Protein Evolution by Recursive Genetic Recombination: Applications to Therapeutic Proteins." *Current Opinion in Biotechnology* 12:361-370 (2001).
Langer, R. et al. "Biocompatibility of Polymeric Delivery Systems for Macromolecules." *J. Biomed. Mater. Res.* 15:267-277 (1981).
Langer, R. "Controlled Release of Macromolecules." *Chemtech* 12:98-105 (1982).
Porter, S. "Human Immune Response to Recombinant Human Proteins." *J. Pharmaceutical Sciences* 90(1):1-11 (2001).
Rosenberg, J.J. et al. "Development of a Novel, Nonimmunogenic, Soluble Human TNF Receptor Type I (sTNFR-I) Construct in the Baboon." *J. Appl. Physiol.* 91:2213-2223 (2001).
Rosenberg, A.S. "Immunogenicity of Biological Therapeutics: A Hierarchy of Concerns." *Immunogenicity of Therapeutic Biological Products, Dev. Biol. Basel, Karger* 112:15-21 (2003).

(Continued)

Primary Examiner—Ilia Ouspenski
(74) Attorney, Agent, or Firm—Perkins Coie LLP

(57) ABSTRACT

Methods and compositions for modulating an immune response to an immunogenic therapeutic agent are disclosed. One of the disclosed methods comprises administering an effective amount of CTLA-4 to decrease the incidence of an immune reaction in conjunction with the administration of a potentially immunogenic substance. Another method contemplates tolerizing a subject to a therapeutic molecule that is or is capable of being immunogenic by the administration of CTLA-4. Various embodiments of CTLA-4 are also disclosed.

21 Claims, 4 Drawing Sheets

OTHER PUBLICATIONS

Schellekens, H. et al. "Immunogenicity of Biopharmaceuticals. The European Perspective." *Immunogenicity of Therapeutic Biological Products, Dev. Biol. Basel, Karger,* 112:23-38 (2003).

Schroff, R.W. et al. "Human Anti-Murine Immunoglobulin Responses in Patients Receiving Monoclonal Antibody Therapy." *Cancer Res.* 45(2):879-885 (1985).

Sidman, K.R. et al. "Controlled Release of Macromolecules and Pharmaceuticals from Synthetic Polypeptides Based on Glutamic Acid." *Biopolymers* 22:547-556 (1983).

Stein, K.E. "Immunogenicity: Concepts/Issues/Concerns." *Biologics 2000—Comparability of Biotechnology Products Dev. Bio. Basel, Karger* 109:15-23 (2002).

Tsutsumi, Y. et al. "Site-Specific Chemical Modification with Polyethylene Glycol of Recombinant Immunotoxin Anti-Tac(Fv)-PE38 (LMB-2) Improves Antitumor Activity and Reduces Animal Toxicity and Immunogenicity." *Proc. Natl. Acad. Sci.* 97:8548-8553 (2000).

* cited by examiner

SEQUENCE LISTING

```
<160> NUMBER OF SEQ ID NOS: 6

<210> SEQ ID NO 1
<211> LENGTH: 186
<212> TYPE: PRT
<213> ORGANISM: Homo sapiens
<220> FEATURE:
<221> NAME/KEY: MISC_FEATURE
<223> OTHER INFORMATION: Full-lenth human CTLA-4 amino acid sequence

<400> SEQUENCE: 1

Met His Val Ala Gln Pro Ala Val Val Leu Ala Ser Ser Arg Gly Ile
1               5                   10                  15

Ala Ser Phe Val Cys Glu Tyr Ala Ser Pro Gly Lys Ala Thr Glu Val
            20                  25                  30

Arg Val Thr Val Leu Arg Gln Ala Asp Ser Gln Val Thr Glu Val Cys
        35                  40                  45

Ala Ala Thr Tyr Met Met Gly Asn Glu Leu Thr Phe Leu Asp Asp Ser
    50                  55                  60

Ile Cys Thr Gly Thr Ser Ser Gly Asn Gln Val Asn Leu Thr Ile Gln
65                  70                  75                  80

Gly Leu Arg Ala Met Asp Thr Gly Leu Tyr Ile Cys Lys Val Glu Leu
                85                  90                  95

Met Tyr Pro Pro Pro Tyr Tyr Leu Gly Ile Gly Asn Gly Thr Gln Ile
            100                 105                 110

Tyr Val Ile Asp Pro Glu Pro Cys Pro Asp Ser Asp Phe Leu Leu Trp
        115                 120                 125
```

```
Ile Leu Ala Ala Val Ser Ser Gly Leu Phe Phe Tyr Ser Phe Leu Leu
            130                 135                 140
Thr Ala Val Ser Leu Ser Lys Met Leu Lys Lys Arg Ser Pro Leu Thr
145                 150                 155                 160
Thr Gly Val Tyr Val Lys Met Pro Pro Thr Glu Pro Glu Cys Glu Lys
                165                 170                 175
Gln Phe Gln Pro Tyr Phe Ile Pro Ile Asn
            180                 185
```

<210> SEQ ID NO 2
<211> LENGTH: 483
<212> TYPE: DNA
<213> ORGANISM: Homo sapiens
<220> FEATURE:
<221> NAME/KEY: misc_feature
<223> OTHER INFORMATION: Nucleic acid encoding 30kDa TNF Inhibitor

<400> SEQUENCE: 2

```
gatagtgtgt gtccccaagg aaaatatatc caccctcaaa ataattcgat ttgctgtacc     60
aagtgccaca aaggaaccta cttgtacaat gactgtccag gcccggggca ggatacggac    120
tgcagggagt gtgagagcgg ctccttcacc gcttcagaaa accacctcag acactgcctc    180
agctgctcca atgccgaaaa ggaaatgggt caggtggaga tctcttcttg cacagtggac    240
cgggacaccg tgtgtggctg caggaagaac cagtaccggc attattggag tgaaaacctt    300
ttccagtgct tcaattgcag cctctgcctc aatgggaccg tgcacctctc ctgccaggag    360
aaacagaaca ccgtgtgcac ctgccatgca ggtttctttc taagagaaaa cgagtgtgtc    420
tcctgtagta actgtaagaa aagcctggag tgcacgaagt tgtgcctacc ccagattgag    480
aat                                                                   483
```

<210> SEQ ID NO 3
<211> LENGTH: 161
<212> TYPE: PRT
<213> ORGANISM: Homo sapiens
<220> FEATURE:
<221> NAME/KEY: MISC_FEATURE
<223> OTHER INFORMATION: 30kDa TNF Inhibitor

<400> SEQUENCE: 3

```
Asp Ser Val Cys Pro Gln Gly Lys Tyr Ile His Pro Gln Asn Asn Ser
1               5                   10                  15
Ile Cys Cys Thr Lys Cys His Lys Gly Thr Tyr Leu Tyr Asn Asp Cys
            20                  25                  30
Pro Gly Pro Gly Gln Asp Thr Asp Cys Arg Glu Cys Glu Ser Gly Ser
        35                  40                  45
Phe Thr Ala Ser Glu Asn His Leu Arg His Cys Leu Ser Cys Ser Lys
    50                  55                  60
Cys Arg Lys Glu Met Gly Gln Val Glu Ile Ser Ser Cys Thr Val Asp
65                  70                  75                  80
Arg Asp Thr Val Cys Gly Cys Arg Lys Asn Gln Tyr Arg His Tyr Trp
                85                  90                  95
Ser Glu Asn Leu Phe Gln Cys Phe Asn Cys Ser Leu Cys Leu Asn Gly
            100                 105                 110
Thr Val His Leu Ser Cys Gln Glu Lys Gln Asn Thr Val Cys Thr Cys
        115                 120                 125
His Ala Gly Phe Phe Leu Arg Glu Asn Glu Cys Val Ser Cys Ser Asn
    130                 135                 140
```

```
Cys Lys Lys Ser Leu Glu Cys Thr Lys Leu Cys Leu Pro Gln Ile Glu
145                 150                 155                 160

Asn
```

<210> SEQ ID NO 4
<211> LENGTH: 223
<212> TYPE: PRT
<213> ORGANISM: Mus musculus
<220> FEATURE:
<221> NAME/KEY: MISC_FEATURE
<223> OTHER INFORMATION: Murine CTLA-4

<400> SEQUENCE: 4

```
Met Ala Cys Leu Gly Leu Arg Arg Tyr Lys Ala Gln Leu Gln Leu Pro
1               5                   10                  15

Ser Arg Thr Trp Pro Phe Val Ala Leu Thr Leu Leu Phe Ile Pro
            20                  25                  30

Val Phe Ser Glu Ala Ile Gln Val Thr Gln Pro Ser Val Val Leu Ala
            35                  40                  45

Ser Ser His Gly Val Ala Ser Phe Pro Cys Glu Tyr Ser Pro Ser His
50                  55                  60

Asn Thr Asp Glu Val Arg Val Thr Val Leu Arg Gln Thr Asn Asp Gln
65                  70                  75                  80

Met Thr Glu Val Cys Ala Thr Thr Phe Thr Glu Lys Asn Thr Val Gly
                85                  90                  95

Phe Leu Asp Tyr Pro Phe Cys Ser Gly Thr Phe Asn Glu Ser Arg Val
            100                 105                 110

Asn Leu Thr Ile Gln Gly Leu Arg Ala Val Asp Thr Gly Leu Tyr Leu
        115                 120                 125

Cys Lys Val Glu Leu Met Tyr Pro Pro Pro Tyr Phe Val Gly Met Gly
    130                 135                 140

Asn Gly Thr Gln Ile Tyr Val Ile Asp Pro Glu Pro Cys Pro Asp Ser
145                 150                 155                 160

Asp Phe Leu Leu Trp Ile Leu Val Ala Val Ser Leu Gly Leu Phe Phe
                165                 170                 175

Tyr Ser Phe Leu Val Ser Ala Val Ser Leu Ser Lys Met Leu Lys Lys
            180                 185                 190

Arg Ser Pro Leu Thr Thr Gly Val Tyr Val Lys Met Pro Pro Thr Glu
        195                 200                 205

Pro Glu Cys Glu Lys Gln Phe Gln Pro Tyr Phe Ile Pro Ile Asn
    210                 215                 220
```

<210> SEQ ID NO 5
<211> LENGTH: 255
<212> TYPE: PRT
<213> ORGANISM: Artificial
<220> FEATURE:
<223> OTHER INFORMATION: Fc fusion protein construct described in
      specification
<220> FEATURE:
<221> NAME/KEY: MISC_FEATURE
<223> OTHER INFORMATION: NGF Peptibody mL63.9

<400> SEQUENCE: 5

```
Met Gln Leu Gly Lys Leu Gln Cys Glu Leu Ser Thr Ala Gly Cys Pro
1               5                   10                  15

Asp Leu Pro Tyr Val Leu Glu Gly Gly Gly Gly Asp Lys Thr His
            20                  25                  30

Thr Cys Pro Pro Cys Pro Ala Pro Glu Leu Leu Gly Gly Pro Ser Val
```

-continued

```
                35                  40                  45
Phe Leu Phe Pro Pro Lys Pro Lys Asp Thr Leu Met Ile Ser Arg Thr
             50                  55                  60

Pro Glu Val Thr Cys Val Val Asp Val Ser His Glu Asp Pro Glu
 65                  70                  75                  80

Val Lys Phe Asn Trp Tyr Val Asp Gly Val Glu Val His Asn Ala Lys
                 85                  90                  95

Thr Lys Pro Arg Glu Glu Gln Tyr Asn Ser Thr Tyr Arg Val Val Ser
                100                 105                 110

Val Leu Thr Val Leu His Gln Asp Trp Leu Asn Gly Lys Glu Tyr Lys
            115                 120                 125

Cys Lys Val Ser Asn Lys Ala Leu Pro Ala Pro Ile Glu Lys Thr Ile
130                 135                 140

Ser Lys Ala Lys Gly Gln Pro Arg Glu Pro Gln Val Tyr Thr Leu Pro
145                 150                 155                 160

Pro Ser Arg Asp Glu Leu Thr Lys Asn Gln Val Ser Leu Thr Cys Leu
                165                 170                 175

Val Lys Gly Phe Tyr Pro Ser Asp Ile Ala Val Glu Trp Glu Ser Asn
            180                 185                 190

Gly Gln Pro Glu Asn Asn Tyr Lys Thr Thr Pro Pro Val Leu Asp Ser
        195                 200                 205

Asp Gly Ser Phe Phe Leu Tyr Ser Lys Leu Thr Val Asp Lys Ser Arg
    210                 215                 220

Trp Gln Gln Gly Asn Val Phe Ser Cys Ser Val Met His Glu Ala Leu
225                 230                 235                 240

His Asn His Tyr Thr Gln Lys Ser Leu Ser Leu Ser Pro Gly Lys
                245                 250                 255

<210> SEQ ID NO 6
<211> LENGTH: 259
<212> TYPE: PRT
<213> ORGANISM: Artificial
<220> FEATURE:
<223> OTHER INFORMATION: Fc fusion protein construct described in
      specification
<220> FEATURE:
<221> NAME/KEY: MISC_FEATURE
<223> OTHER INFORMATION: NGF Peptibody mL6-17

<400> SEQUENCE: 6

Met Asp Lys Thr His Thr Cys Pro Pro Cys Pro Ala Pro Glu Leu Leu
 1               5                  10                  15

Gly Gly Pro Ser Val Phe Leu Phe Pro Pro Lys Pro Lys Asp Thr Leu
                20                  25                  30

Met Ile Ser Arg Thr Pro Glu Val Thr Cys Val Val Val Asp Val Ser
            35                  40                  45

His Glu Asp Pro Glu Val Lys Phe Asn Trp Tyr Val Asp Gly Val Glu
        50                  55                  60

Val His Asn Ala Lys Thr Lys Pro Arg Glu Glu Gln Tyr Asn Ser Thr
 65                 70                  75                  80

Tyr Arg Val Val Ser Val Leu Thr Val Leu His Gln Asp Trp Leu Asn
                85                  90                  95

Gly Lys Glu Tyr Lys Cys Lys Val Ser Asn Lys Ala Leu Pro Ala Pro
            100                 105                 110

Ile Glu Lys Thr Ile Ser Lys Ala Lys Gly Gln Pro Arg Glu Pro Gln
        115                 120                 125
```

-continued

```
Val Tyr Thr Leu Pro Pro Ser Arg Asp Glu Leu Thr Lys Asn Gln Val
    130                 135                 140

Ser Leu Thr Cys Leu Val Lys Gly Phe Tyr Pro Ser Asp Ile Ala Val
145                 150                 155                 160

Glu Trp Glu Ser Asn Gly Gln Pro Glu Asn Asn Tyr Lys Thr Thr Pro
                165                 170                 175

Pro Val Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
            195                 200                 205

Met His Glu Ala Leu His Asn His Tyr Thr Gln Lys Ser Leu Ser Leu
    210                 215                 220

Ser Pro Gly Lys Gly Gly Gly Gly Ala Gln Met Ile Asp Trp Leu
225                 230                 235                 240

Ser Gln Asn Arg Leu Phe Glu Gln Tyr Phe Glu Leu Ile Pro Pro Gly
                245                 250                 255

Val Leu Glu
```

COMPOSITIONS AND METHODS TO MODULATE AN IMMUNE RESPONSE TO AN IMMUNOGENIC THERAPEUTIC AGENT

PRIORITY CLAIM

The present application is a continuation of PCT/US04/35415, filed Oct. 26, 2004, which application claims the benefit of U.S. Provisional Application No. 60/515,199, filed Oct. 27, 2003, both of which are hereby incorporated by reference in their entirety including drawings as fully set forth herein.

FIELD OF THE INVENTION

The present invention is generally in the field of immunology and of modulating response to immunogenic therapeutic agents.

BACKGROUND OF THE INVENTION

The use of recombinant proteins and other large molecules for diagnosis and therapy has been one of the greatest achievements of biotechnology. According to some reports, nearly 20 recombinant human protein pharmaceuticals have been approved for clinical use. Porter, S., Journal of Pharmaceutical Sciences 90(1):1-11 (2001). Biological medicinal products and therapeutic agents have become a growing proportion of tested pharmaceutical drugs.

Even with the demonstrated success of recombinant proteins, antibodies and other large molecules in therapeutic and diagnostic applications, there has been a concern that the delivery of pharmacological proteins to individuals would induce an immune response, especially when the protein is provided in multiple doses over a period of time. Koren, et al., Current Pharmaceutical Biotechnology 3(4):349-360 (2002) present a table (table 1 at p. 352-3) detailing the incidence and clinical sequelae of antibody responses to some therapeutic proteins. Porter, supra, also provides a summary of the actual reported observations regarding human immune response to administered doses of recombinant human proteins.

Three categories of immune reactions have been reviewed in Rosenberg, A. S., Immunogenicity of Therapeutic Biological Products, Dev. Biol. Basel 112, pp. 15-212 (2003).

A first type of immune reaction, immediate hypersensitivity responses that may cause anaphylactic or anaphylactoid responses, has presented the greatest concern. This type of immune reaction is rare, however. It has most frequently been linked to recurrent administration of bacterial proteins which lack a mammalian counterpart. Id.

A second type of immune reaction is characterized by the formation of antibodies that neutralize not only the therapeutic agent but also endogenous factors. Thus, this type of immune reaction has the potential of causing serious adverse consequences. Rosenberg, supra.

Lastly, there has been the concern that the generation of binding antibodies may cause invasion reactions, alter pharmacokinetics and biodistribution, and potentially diminish product efficacy. For example, antibodies to primatized, chimeric or humanized antibody therapeutics like infleximab, retuximab, and the like, have been observed in patients.

Several factors may impact the generation of immune responses to therapeutic proteins (particularly the non-self portion of a therapeutic protein), including the immunogenicity of recombinant proteins, the presence of impurities, product aggregation, dose, route and frequency of administration. Rosenberg supra.

Cytokines are one of the classes of proteins whose use as therapeutic agents have encountered safety and efficacy issues due to their actual and potential immunogenicity. Reviewed in Herzyk, D. J., Current Opinion in Molecular Therapeutics 5(2):167-171 (2003).

Antibodies, diabodies, and other such immunoglobulin-like molecules used for imaging and therapy have also encountered issues with actual and potential immunogenicity.

Several approaches have been advanced with varying success in an effort to decrease the immunogenicity of immunogenic therapeutic molecules, many of which involve further manipulations of the therapeutic molecule. Such approaches include de-immunization, Issacs, J D, Rheumatology 40:724-738 (2001), gene-shuffling, Kurtzman, et al., Curr Opin Biotechnol 12:361-370 (2001); Chang, et al., Nat Biotechnol 17:793-797 (1999), pegylation, Rosemberg, et al., J App Physiol 91:2213-2223 (2001); Tsutsumi, et al., Proc Natl Acad Sci 97:8548-8553 (2000), and producing IgG molecules having a human sequence in transgenic mice, Davis, et al., Cancer and Metastasis Reviews 18:421-425 (1999); Green, et al., J Immunol Meth 231:11-23 (1999). Such approaches are most likely to be successful at reducing an immunogenic response when the mechanism by which the therapeutic molecule induces the response is known. Even if successful, the approaches will involve considerable delay in the development and approval of a therapeutic molecule for use in humans.

Accordingly, there is a need for safe and effective compositions and methods to decrease the probability of incidence of an immune reaction to immunogenic therapeutic molecules, and to decrease antibody production when said immune reactions do occur.

BRIEF SUMMARY OF THE INVENTION

In a first embodiment the present invention pertains to a method for decreasing the probability of the incidence of an immune reaction when a subject is administered a therapeutic composition having an otherwise immunogenic therapeutic molecule. The method includes administering to a subject an effective amount of an effective form of CTLA-4 within an effective time interval relative to the administration of said therapeutic composition.

In a second embodiment, the present invention pertains to a composition that includes a therapeutic molecule capable of producing an immune response and an effective form of CTLA-4.

In a third embodiment, administration of CTLA-4 in accordance with the present invention decreases the probability of an incidence of an immune reaction against an immunogenic therapeutic molecule.

In a fourth embodiment, administration of CTLA-4 in accordance with the present invention induces immune tolerance to an immunogenic therapeutic molecule.

In a fifth embodiment, administration of CTLA-4 in accordance with the present invention decreases the amount of antibodies generated to an immunogenic therapeutic molecule, thus lessening the severity of an immune reaction.

DETAILED DESCRIPTION OF THE INVENTION

Figure 1:
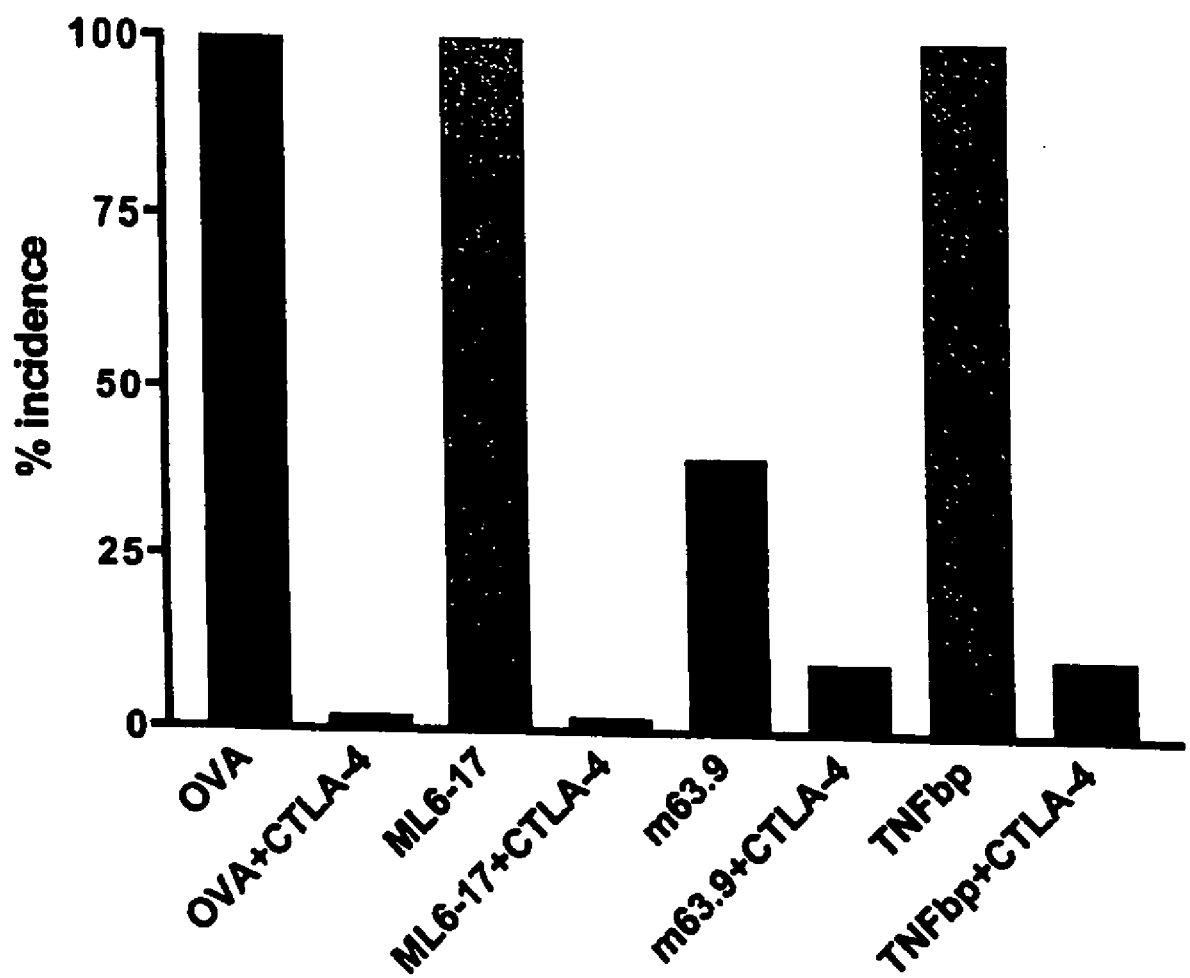
FIG. 1 shows the antibody response in various groups of mice challenged from day 30 to 40 with an immunogenic composition that had previously been administered either alone or in combination with CTLA-4.

As used herein, the term "statistically significant" has the same meaning it has in the art, e.g., that an observed effect is unlikely the result of mere chance. P values, or the like, may be used in this context, in which case a $p<0.5$ may indicate a statistically significant result. Other preferred p values include $<0.2$, $<0.1$, $<0.05$ and $<0.01$, although other p values may be used in accordance with accepted practices in the art.

Administration of CTLA-4 in accordance with the present invention decreases the probability of an incidence of an immune reaction against an immunogenic therapeutic molecule.

In another embodiment, administration of CTLA-4 in accordance with the present invention induces immune tolerance to an immunogenic therapeutic molecule.

In another embodiment, administration of CTLA-4 in accordance with the present invention decreases mean antibodies titers to an immunogenic therapeutic molecule.

It has been found that CTLA-4, when administered in an effective time interval relative to the administration of an immunogenic therapeutic molecule, induces tolerance to and decreases immunogenicity of said therapeutic molecule in a specific manner. Administration of CTLA-4 induces tolerance to an immunogenic therapeutic molecule with which it is administered, but not to another immunogenic therapeutic molecule administered at some other time.

In accordance with the present invention the probability that an immune response will be elicited by the immunogenic therapeutic molecule may be decreased such that the probability is no greater than about 1%. In accordance with the present invention the probability that an immune response will be elicited by the immunogenic therapeutic molecule may be decreased such that the probability is no greater than about 5%. In accordance with the present invention the probability that an immune response will be elicited by the immunogenic therapeutic molecule may be decreased such that the probability is no greater than about 10%. In accordance with the present invention the probability that an immune response will be elicited by the immunogenic therapeutic molecule may be decreased such that the probability is no greater than about 20%. In accordance with the present invention the probability that an immune response will be elicited by the immunogenic therapeutic molecule may be decreased such that the probability is no greater than about 30%. In accordance with the present invention the probability that an immune response will be elicited by the immunogenic therapeutic molecule may be decreased such that the probability is no greater than about 40%. In accordance with the present invention the probability that an immune response will be elicited by the immunogenic therapeutic molecule may be decreased such that the probability is no greater than about 50%. In accordance with the present invention the probability that an immune response will be elicited by the immunogenic therapeutic molecule may be decreased such that the probability is no greater than about 60%. In accordance with the present invention the probability that an immune response will be elicited by the immunogenic therapeutic molecule may be decreased such that the probability is no greater than about 70%. In accordance with the present invention the probability that an immune response will be elicited by the immunogenic therapeutic molecule may be decreased such that the probability is no greater than about 80%. In accordance with the present invention the probability that an immune response will be elicited by the immunogenic therapeutic molecule may be decreased such that the probability is no greater than about 90%.

In accordance with the present invention, immune tolerance to an immunogenic therapeutic molecule ("tolerance") may be developed in at least about 10% of the subjects. In accordance with the present invention, tolerance may be developed in at least about 20% of the subjects. In accordance with the present invention, tolerance may be developed in at least about 30% of the subjects. In accordance with the present invention, tolerance may be developed in at least about 40% of the subjects. In accordance with the present invention, tolerance may be developed in at least about 50% of the subjects. In accordance with the present invention, tolerance may be developed in at least about 60% of the subjects. In accordance with the present invention, tolerance may be developed in at least about 70% of the subjects. In accordance with the present invention, tolerance may be developed in at least about 80% of the subjects. In accordance with the present invention, tolerance may be developed in at least about 90% of the subjects.

In accordance with the present invention, antibody titers may be decreased at least by about 10% when compared to a control. In accordance with the present invention, antibody titers may be decreased at least by about 20% when compared to a control. In accordance with the present invention, antibody titers may be decreased at least by about 30% when compared to a control. In accordance with the present invention, antibody titers may be decreased at least by about 40% when compared to a control. In accordance with the present invention, antibody titers may be decreased at least by about 50% when compared to a control. In accordance with the present invention, antibody titers may be decreased at least by about 60% when compared to a control. In accordance with the present invention, antibody titers may be decreased at least by about 70% when compared to a control. In accordance with the present invention, antibody titers may be decreased at least by about 80% when compared to a control. In accordance with the present invention, antibody titers may be decreased at least by about 90% when compared to a control.

Any effective form of CTLA-4 may be used in accordance with the present invention. The CTLA-4 form used is preferably from the same species. In another embodiment, immune tolerizing agents other than inhibitors and/or modulators of the CD28/B7 pathway may also be used either independently or in combination with CTLA-4 in accordance with the teachings of the present invention.

The term "CTLA-4" refers to a protein having an amino acid sequence as shown in SEQ ID NO: 1, or fragments thereof, including soluble forms of CTLA-4 such as an extracellular domain of CTLA-4 or a fragment thereof. "CTLA-4" also refers to a protein having an amino acid sequence as shown in SEQ ID NO: 4, or fragments thereof, including soluble forms as set forth above. CTLA-4 may also be linked to a vehicle in order to enhance the activity, half-life, solubility, and so forth of the molecule.

The term "vehicle" refers to a molecule that prevents degradation and/or increases half-life, reduces toxicity, or increases biological activity of a therapeutic protein. Exemplary vehicles include an Fc domain, a linear polymer (e.g., polyethylene glycol (PEG), polylysine, dextran, etc.); a branched-chain polymer (see, for example, U.S. Pat. No. 4,289,872 to Denkenwalter et al., issued Sep. 15, 1981; U.S. Pat. No. 5,229,490 to Tam, issued Jul. 20, 1993; WO 93/21259 by Frechet et al., published 28 Oct. 1993); a lipid; a cholesterol group (such as a steroid); a carbohydrate or oligosaccharide (e.g., dextran); or any natural or synthetic protein, polypeptide or peptide that binds to a salvage receptor.

In one embodiment CTLA-4 is fused to a human immunoglobulin region either directly or through one or more linker moieties. In another embodiment, CTLA-4 comprises an extracellular domain of CTLA-4 which binds B7.1 and/or B7.2 and partially or completely inhibits immune responses mediated by the CD28/B7 pathway. In one embodiment, a CTLA-4 extracellular domain comprises about amino acid residues 1 (methionine) to 124 (aspartic acid) as shown in SEQ ID NO: 1. Other CTLA-4 polypeptides useful in the invention include fragments which encompass at least a portion of a CTLA-4 extracellular domain, which fragments bind B7.1 and/or B7.2 and partially or completely inhibit immune responses mediated by the CD28/B7 pathway. A CTLA-4 extracellular domain may also be fused to a human immunoglobulin region either directly or through one or more linker moieties.

In another embodiment, CTLA-4 polypeptides include variants having a substitution, deletion or insertion of one or more amino acids in the sequence shown in SEQ ID NO: 1. As examples, a CTLA-4 variant may have a substitution of a different amino acid for serine at position 25, alanine at position 29, threonine at position 30, leucine at position 104 and/or glycine at position 105. In certain embodiments, CTLA-4 variants are as described in PCT publication No. WO 02/02638. In one embodiment, a CTLA-4 variant has a tyrosine substituted for an alanine at position 29 and a glutamic acid substituted for a leucine at position 104 of the sequences shown in SEQ ID NO: 1. Examples of other CTLA-4 variants are described in PCT publication Nos. WO 98/33513 and WO 01/92337. In other embodiments, the above-mentioned CTLA-4 variants are in the extracellular domain of about residues 1-124 fused to an immunoglobulin constant region such as an Fc domain.

The term "Fc domain" or "Fc" refers to molecule or sequence comprising the sequence of a non-antigen-binding fragment of a whole antibody, whether in monomeric or multimeric form. An "Fc domain" or "Fc" may include a "native Fc" or an "Fc variant". The original immunoglobulin source of the native Fc is preferably of human origin and may be any of the immunoglobulins, although IgG1 and IgG2 are preferred. Native Fc's are made up of monomeric polypeptides that may be linked into dimeric or multimeric forms by covalent (i.e., disulfide bonds) and non-covalent association. The number of intermolecular disulfide bonds between monomeric subunits of native Fc molecules ranges from 1 to 4 depending on class (e.g., IgG, IgA, IgE) or subclass (e.g., IgG1, IgG2, IgG3, IgA1, IgGA2). One example of a native Fc is a disulfide-bonded dimer resulting from papain digestion of an IgG (see Ellison et al. (1982), *Nucleic Acids Res.* 10: 4071-9). The term "native Fc" as used herein is generic to the monomeric, dimeric, and multimeric forms. The term "Fc variant" refers to a molecule or sequence that is modified from a native Fc but still comprises a binding site for the salvage receptor, FcRn. International applications WO 97/34631 (published 25 Sep. 1997) and WO 96/32478 describe exemplary Fc variants, as well as interaction with the salvage receptor, and are hereby incorporated by reference.

The Fc may be bound in any effective place of the protein, including, for example at the N terminus or at the C terminus. The Fc may also be bound elsewhere directly onto the protein or via an effective linker.

CTLA-4 may be administered in any effective manner. An effective manner is any manner that provides a statistically significant modulation of the immune response in accordance with an embodiment of the present invention. An effective manner of administration can be determined by those of skill in the art in accordance with the teachings provided herein, while also taking into consideration the condition to be treated, the immunogenic therapeutic molecule to be administered, the form, dose, pharmacokinetic characteristics, manner and regimen of CTLA-4 and immunogenic therapeutic molecule administrated, the age and condition of the subject, and other variables known to those of skill in the art.

CTLA-4 may be administered in any effective dose. Unless otherwise specified or required by the context, as used herein an effective dose of CTLA-4 is any dose that provides a statistically significant modulation of the immune response in accordance with an embodiment of the present invention. An effective dose can be determined by those of skill in the art in accordance with the teachings provided herein, while also taking into consideration the condition to be treated, the immunogenic therapeutic molecule to be administered, the form, dose, pharmacokinetic characteristics, manner and regimen of CTLA-4 and immunogenic therapeutic molecule administrated, the age and condition of the subject, and other variables known to those of skill in the art.

The effective amount of a CTLA-4 pharmaceutical composition to be employed therapeutically will depend, for example, upon the therapeutic context and objectives. One skilled in the art will appreciate that the appropriate dosage levels for treatment will vary depending, in part, upon the CTLA-4 molecule delivered, the nature of the immunogenic response for which CTLA-4 is being used, the route of administration, and the size (body weight, body surface or organ size) and/or condition (the age and general health) of the patient. In certain embodiments, clinicians may titer the dosage and modify the route of administration to obtain the optimal therapeutic effect. A typical dosage may range from about 0.1 µg/kg to up to about 100 mg/kg or more, depending on the factors mentioned above. In preferred embodiments, the dosage may range from 0.1 µg/kg up to about 30 mg/kg; more preferably from 1 µg/kg up to about 30 mg/kg; or even more preferably from 5 µg/kg up to about 30 mg/kg.

CTLA-4 may be administered in any effective regimen. An effective regimen is any regimen that provides a statistically significant modulation of the immune response in accordance with an embodiment of the present invention. An effective regimen of administration can be determined by those of skill in the art in accordance with the teachings provided herein, while also taking into consideration the condition to be treated, the immunogenic therapeutic molecule to be administered, the form, dose, pharmacokinetic characteristics, manner and regimen of CTLA-4 and immunogenic therapeutic molecule administrated, the age and condition of the subject, and other variables known to those of skill in the art. The CTLA-4 may be administered prior to administration of the immunogenic therapeutic molecule, after administration of the immunogenic therapeutic molecule or contemporaneous with the administration of the immunogenic therapeutic molecule. In addition, the CTLA-4 may be administered more, less, or the same amount of times as the immunogenic therapeutic molecule.

Dosing frequency will depend upon the pharmacokinetic parameters of the particular CTLA-4 molecule composition being used and the pharmacokinetic parameters of the particular immunogenic therapeutic molecule being used. Typically, a clinician administers the composition until a dosage is reached that achieves the desired effect. The composition may therefore be administered as a single dose, or as two or more doses (which may or may not contain the same amount of the desired molecule) over time, or as a continuous infusion via an implantation device or catheter. Further refinement of the appropriate dosage is routinely made by those of ordinary skill in the art and is within the ambit of tasks routinely performed by them. Appropriate dosages may be ascertained through use of appropriate dose-response data.

The compositions of the present invention may be formulated in any effective manner. An effective formulation for the administration of CTLA-4 and the immunogenic therapeutic molecule can be determined by those of skill in the art in accordance with the teachings provided herein, while also taking into consideration the condition to be treated, the immunogenic therapeutic molecule to be administered, the form, dose, pharmacokinetic characteristics, manner and regimen of CTLA-4 and immunogenic therapeutic molecule administrated, the age and condition of the subject, and other variables known to those of skill in the art. The route of administration of the pharmaceutical composition is in accord with known methods, e.g. orally, through injection by intravenous, intraperitoneal, intracerebral (intra-parenchymal), intracerebroventricular, intramuscular, intra-ocular, intraarterial, intraportal, or intralesional routes; by sustained release systems or by implantation devices. In certain embodiments, the compositions may be administered by bolus injection or continuously by infusion, or by implantation device.

The composition also may be administered locally via implantation of a membrane, sponge or another appropriate material onto which the desired molecule has been absorbed or encapsulated. In certain embodiments, where an implantation device is used, the device may be implanted into any suitable tissue or organ, and delivery of the desired molecule may be via diffusion, timed-release bolus, or continuous administration.

It also may be desirable to use CTLA-4 pharmaceutical compositions according to the invention ex vivo. In such instances, cells, tissues or organs that have been removed from the patient are exposed to CTLA-4 pharmaceutical compositions after which the cells, tissues and/or organs are subsequently implanted back into the patient.

In particular, CTLA-4 can be delivered by implanting certain cells that have been genetically engineered, using methods such as those known in the art, to express and secrete the polypeptide. In other embodiments, such cells may be animal or human cells, and may be autologous, heterologous, or xenogeneic. In other embodiments, the cells may be immortalized.

In one embodiment, CTLA-4 may be administered with an immunogenic therapeutic molecule until tolerance is formed to the immunogenic therapeutic molecule. The immunogenic therapeutic molecule may then continue to be administered without CTLA-4 until the tolerance weakens or ceases. Tolerance may be reinforced by repeating the administration of CTLA-4 with the immunogenic therapeutic molecule. In another embodiment, CTLA-4 may be continuously administered with the immunogenic therapeutic molecule.

In other embodiments, the invention provides pharmaceutical compositions comprising an effective amount of CTLA-4 together with a pharmaceutically acceptable diluent, carrier, solubilizer, emulsifier, preservative and/or adjuvant. Acceptable formulation materials are nontoxic to recipients at the dosages and concentrations employed. In another embodiment, pharmaceutical compositions comprising an effective amount of CTLA-4-Fc are provided.

In another embodiment, the invention provides pharmaceutical compositions comprising an effective amount of CTLA-4 and an effective amount of an immunogenic therapeutic molecule together with a pharmaceutically acceptable diluent, carrier, solubilizer, emulsifier, preservative and/or adjuvant. Preferably, acceptable formulation materials are nontoxic to recipients at the dosages and concentrations employed. In another embodiment, pharmaceutical compositions comprising an effective amount of CTLA-4-Fc and an effective amount of an immunogenic therapeutic molecule are provided. In one embodiment, the compositions may be in the form of a mixture of CTLA-4 and the immunogenic therapeutic molecule. The compositions may be an effective form of a single molecule including an effective form of CTLA-4 and an effective form of an immunogenic therapeutic molecule.

In another embodiment, the pharmaceutical composition may contain formulation materials for modifying, maintaining or preserving, for example, the pH, osmolarity, viscosity, clarity, color, isotonicity, odor, sterility, stability, rate of dissolution or release, adsorption or penetration of the composition. In such embodiments, suitable formulation materials include, but are not limited to, amino acids (such as glycine, glutamine, asparagine, arginine or lysine); antimicrobials; antioxidants (such as ascorbic acid, sodium sulfite or sodium hydrogen-sulfite); buffers (such as borate, bicarbonate, Tris-HCl, citrates, phosphates or other organic acids); bulking agents (such as mannitol or glycine); chelating agents (such as ethylenediamine tetraacetic acid (EDTA)); complexing agents (such as caffeine, polyvinylpyrrolidone, beta-cyclodextrin or hydroxypropyl-beta-cyclodextrin); fillers; monosaccharides; disaccharides; and other carbohydrates (such as glucose, mannose or dextrins); proteins (such as serum albumin, gelatin or immunoglobulins); coloring, flavoring and diluting agents; emulsifying agents; hydrophilic polymers (such as polyvinylpyrrolidone); low molecular weight polypeptides; salt-forming counterions (such as sodium); preservatives (such as benzalkonium chloride, benzoic acid, salicylic acid, thimerosal, phenethyl alcohol, methylparaben, propylparaben, chlorhexidine, sorbic acid or hydrogen peroxide); solvents (such as glycerin, propylene glycol or polyethylene glycol); sugar alcohols (such as mannitol or sorbitol); suspending agents; surfactants or wetting agents (such as pluronics, PEG, sorbitan esters, polysorbates such as polysorbate 20, polysorbate 80, triton, tromethamine, lecithin, cholesterol, tyloxapal); stability enhancing agents (such as sucrose or sorbitol); tonicity enhancing agents (such as alkali metal halides, preferably sodium or potassium chloride, mannitol sorbitol); delivery vehicles; diluents; excipients and/or pharmaceutical adjuvants. See Remington's Pharmaceutical Sciences, 18$^{th}$ Edition, (A. R. Gennaro, ed.), 1990, Mack Publishing Company.

In other embodiments, the optimal pharmaceutical composition will be determined by one skilled in the art depending upon, for example, the intended route of administration, delivery format and desired dosage. See, for example, Remington's Pharmaceutical Sciences, supra. In other embodiments, such compositions may influence the physical state, stability, rate of in vivo release and rate of in vivo clearance of CTLA-4.

In other embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In preferred embodiments, pharmaceutical compositions comprise Tris buffer of about pH 7.0-8.5, or acetate buffer of about pH 4.0-5.5, and may further include sorbitol or a suitable substitute therefor. In other embodiments of the invention, CTLA-4 compositions may be prepared for storage by mixing the selected composition having the desired degree of purity with optional formulation agents (Remington's Pharmaceutical Sciences, supra) in the form of a lyophilized cake or an aqueous solution. Further, in certain embodiments, CTLA-4 may be formulated as a lyophilizate using appropriate excipients such as sucrose.

The pharmaceutical compositions of the invention can be selected for parenteral delivery. Alternatively, the compositions may be selected for inhalation or for delivery through the digestive tract, such by ingestion. Preparation of such pharmaceutically acceptable compositions is within the skill of the art.

The formulation components are present preferably in concentrations that are acceptable to the site of administration. In certain embodiments, buffers are used to maintain the composition at physiological pH or at a slightly lower pH, typically within a pH range of from about 5 to about 8.

When parenteral administration is contemplated, the therapeutic compositions for use in this invention may be provided in the form of a pyrogen-free, parenterally acceptable aqueous solution comprising CTLA-4 in a pharmaceutically acceptable vehicle. A particularly suitable vehicle for parenteral injection is sterile distilled water in which CTLA-4 is formulated as a sterile, isotonic solution, which is properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired molecule.

Pharmaceutical compositions of the invention can be formulated for inhalation. In these embodiments, CTLA-4 is advantageously formulated as a dry, inhalable powder. In other embodiments, CTLA-4 inhalation solutions may also be formulated with a propellant for aerosol delivery. In other embodiments, solutions may be nebulized. Pulmonary administration and formulation methods therefore are further described in International Patent Application No. PCT/US94/001875, which is incorporated by reference and describes pulmonary delivery of chemically modified proteins.

It is also contemplated that formulations can be administered orally. CTLA-4 administered in this fashion can be formulated with or without carriers customarily used in the compounding of solid dosage forms such as tablets and capsules. In other embodiments, a capsule may be designed to release the active portion of the formulation at the point in the gastrointestinal tract when bioavailability is maximized and pre-systemic degradation is minimized. Additional agents can be included to facilitate absorption. Diluents, flavorings, low melting point waxes, vegetable oils, lubricants, suspending agents, tablet disintegrating agents, and binders may also be employed.

A pharmaceutical composition of the invention is preferably provided to comprise an effective quantity of CTLA-4 in a mixture with non-toxic excipients that are suitable for the manufacture of tablets. By dissolving the tablets in sterile water, or another appropriate vehicle, solutions may be prepared in unit-dose form. Suitable excipients include, but are not limited to, inert diluents, such as calcium carbonate, sodium carbonate or bicarbonate, lactose, or calcium phosphate; or binding agents, such as starch, gelatin, or acacia; or lubricating agents such as magnesium stearate, stearic acid, or talc.

Additional pharmaceutical compositions will be evident to those skilled in the art, including formulations involving CTLA-4 in sustained or controlled-delivery formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which is incorporated by reference and describes controlled release of porous polymeric microparticles for delivery of pharmaceutical compositions. Sustained-release preparations may include semipermeable polymer matrices in the form of shaped articles, e.g. films, or microcapsules. Sustained release matrices may include polyesters, hydrogels, polylactides (as disclosed in U.S. Pat. No. 3,773,919 and European Patent Application Publication No. EP 058481, each of which is incorporated by reference), copolymers of L-glutamic acid and gamma ethyl-L-glutamate (Sidman et al., 1983, *Biopolymers* 22:547-556), poly (2-hydroxyethyl-methacrylate) (Langer et al., 1981, *J. Biomed. Mater. Res.* 15:167-277 and Langer, 1982, *Chem. Tech.* 12:98-105), ethylene vinyl acetate (Langer et al., supra) or poly- D(-)-3-hydroxybutyric acid (European Patent Application Publication No. EP 133,988). Sustained release compositions may also include liposomes that can be prepared by any of several methods known in the art. See e.g., Eppstein et al., 1985, *Proc. Natl. Acad. Sci. USA* 82:3688-3692; European Patent Application Publication Nos. EP 036,676; EP 088,046 and EP 143,949, incorporated by reference.

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper that is capable of being pierced by a hypodermic injection needle.

Once the pharmaceutical composition has been formulated, it may be stored in sterile vials as a solution, suspension, gel, emulsion, solid, or as a dehydrated or lyophilized powder. Such formulations may be stored either in a ready-to-use form or in a form (e.g., lyophilized) that is reconstituted prior to administration.

The invention also provides kits for producing a single-dose administration unit. The kits of the invention may each contain a first container having a dried protein and a second container having an aqueous formulation. In certain embodiments of this invention, kits containing single and multi-chambered pre-filled syringes (e.g., liquid syringes and lyo-syringes) are provided.

The invention also provides kits for producing a single-dose administration unit for CTLA-4 or the like and a single-dose administration unit for an immunogenic therapeutic molecule. The kits of the invention may each contain both a first container having an effective form of CTLA-4, for example as a dried protein, a second container having an immunogenic therapeutic composition, a third container having an aqueous formulation for the CTLA-4 dried protein and a fourth container having an aqueous formulation for the immunogenic therapeutic composition. Alternatively, the CTLA-4 and the immunogenic therapeutic composition may be soluble in the same aqueous formulation, in which case only a third container is necessary. In certain embodiments of this invention, kits containing single and multi-chambered pre-filled syringes (e.g., liquid syringes and lyosyringes) are provided. Administration of CTLA-4, other immune tolerizing agents, and the like may be used in accordance with the present invention, either alone or in combination, to modulate the immune response against any immunogenic therapeutic molecule for which they are effective.

Unless otherwise required by the context, as used herein the term immunogenic therapeutic molecule means any molecule having a therapeutic or in vivo diagnostic use and that is capable of generating an immune response when administered to a subject. Whether a molecule is capable of generating an immune response may be determined in any effective manner, including empirically, by molecular modeling, structural analysis and the like. See, e.g., Koren, et al., Current Pharmaceutical Biotechnology 3:349-360 (2002).

Immunogenic therapeutic molecules in accordance with an embodiment of the present invention are therapeutic proteins. These include, for example hormones, enzymes, cytokines, antibodies, receptors and antagonists, growth factors, interferons, and the like. See, e.g., Koren, et al., Current Pharmaceutical Biotechnology 3:349-360 (2002); Porter, S., Journal of Pharmaceutical Sciences 90(1):1-11 (2001); Rosenberg, A. S., Immunogenicity of Therapeutic Biological Products, Dev. Biol. Basel, Karger, 2003, vol 112, pp. 15-21; Schellekens, et al., Immunogenicity of Therapeutic Biological Products, Dev. Biol. Basel, Karger, 2003, vol 112, pp. 23-38; Chamberlain, et al., Immunogenicity of Therapeutic Biological Products, Dev. Biol. Basel, Karger, 2003, vol 112, pp. 3-11; Stein, K. F., Biologics 2000—Comparability of Biotechnology Products Dev. Bio. Basel, Karger, 2002, vol. 109, pp. 15-23; Herzyk, D. J., Current Opinion in Molecular Therapeutics 5(2):167-171 (2003); Schroff, et al., Human anti-murine immunoglobulin responses in patients receiving monoclonal antibody therapy, Cancer Res., 45(2):879-85 (1985); Isaacs, J. D., The antiglobulin response to therapeutic antibodies, Semin Immunol., 2(6):449-56 (1990) (all of which are incorporated herein by reference as if fully set forth herein). In other embodiments, at least part of the therapeutic molecules comprises a non-human component. Said non-human component may be from another organism other than a human, such as a mouse, or it may be the product of chemical synthesis, for example, a non-naturally occurring amino acid or a synthetic water soluble polymer.

Unless otherwise required by the context, as used herein the term immune response means that detectable serum antibodies specific for the protein of interest are formed, e.g., an overt presence of detectable antibodies.

Methods for determining whether an immune response to a therapeutic molecule has occurred are known to those in the art. Generally, a convenient method for detecting an immune response is by determining levels of anti-therapeutic antibodies in a patient's sera. Analysis of antibodies in biological fluids may be carried out in any effective manner, including, for example, radioimmunoprecipitation assays (RIA), enzyme linked immunosorbent assays (ELISA), dissociation enhanced lanthanide fluroimmunoassays (DELFIA), and surface plasmon resonance methods. These methods will detect whether an antibody binds to the therapeutic molecule and may also be used to detect whether an antibody will cross-react with other related molecules. For additional details, see Koren et al. supra.

The biological effects of an antibody produced by immune response can most conveniently be determined by a bioassay suitable for the therapeutic molecule being administered. Generally, observing a decreased activity when serum from a patient exhibiting an immune response is added to a bioassay may indicate a neutralizing activity by an antibody.

Specific examples of therapeutic immunogenic molecules described herein include TNFbp and peptides designated mL6-17 and mL63-9 (synthetic peptides which bind to nerve growth factor) fused to an Fc domain. The peptide sequence of the fusion mL63-9-Fc is shown in SEQ ID NO: 5. The peptide sequence of the fusion mL6-17-Fc is shown in SEQ ID NO: 6. TNFbp comprises two 30kDa TNF inhibitor polypeptides, which are covalently attached by a bifunctional 20 kDa polyethylene glycol (PEG) group through a cysteine residue introduced at position 105 of the polypeptide represented in SEQ ID NO:3. (SEQ ID NO: 2 is the nucleic acid sequence and SEQ ID NO:3 is the amino acid sequence.) The substitution of a cysteine residue for an asparagine residue at position 105 was carried out by site-directed mutagenesis as previously described. (See published European patent application EP 0 422 339, WO92/16221 and PCT publication no. WO95/34326). 92/16221 states at page 15: "This invention describes pegylated 30kDa TNF inhibitor and pegylated IL-1 receptor antagonist. Most preferred pegylated TNF inhibitors include 30kDa TNF inhibitor wherein the asparagine amino acid residue at position 105 of the native human protein is changed to cysteine using in vitro mutagenesis and pegylation has occurred at the free cysteine at position 105. Other pegylated derivatives of mutated 30kDa TNF inhibitors include mutations where cysteine has been added at positions 1, 14, 111 and 161. In addition to the singly pegylated muteins, any and all combinations of the various mutations may be included within a single mutein to create altered 30kDa TNF with more than one free cysteine residue capable of being pegylated."

A wide variety of factors can impact on the response of the immune system to a product. Accordingly, in accordance with the present invention the disease type, severity and benefit of treatment should be considered when assessing the risk associated with the immunogenicity of any biological product.

The following sequences are relevant to the present invention:

SEQ ID NO: 1
Full-Length Human CTLA-4 Amino Acid Sequence

```
MHVAQPAVV LASSRGIASF VCEYASPGKA TEVRVTVLRQ ADSQVTEVCA

ATYMMGNELT FLDDSICTGT SSGNQVNLTI QGLRAMDTGL YICKVELMYP

PPYYLGIGNG TQIYVIDPEP CPDSDFLLWI LAAVSSGLFF YSFLLTAVSL

SKMLKKRSPL TTGVYVKMPP TEPECEKQFQ PYFIPIN
```

SEQ ID NO: 2
Nucleic Acid Encoding 30 kDa TNF Inhibitor

```
GATAGTGTGTGTCCCCAAGGAAAATATATCCACCCTCAAAATAATTCGAT

TTGCTGTACCAAGTGCCACAAAGGAACCTACTTGTACAATGACTGTCCAG

GCCCGGGGCAGGATACGGACTGCAGGGAGTGTGAGAGCGGCTCCTTCACC

GCTTCAGAAAACCACCTCAGACACTGCCTCAGCTGCTCCAAATGCCGAAA

GGAAATGGGTCAGGTGGAGATCTCTTCTTGCACAGTGGACCGGGACACCG

TGTGTGGCTGCAGGAAGAACCAGTACCGGCATTATTGGAGTGAAAACCTT

TTCCAGTGCTTCAATTGCAGCCTCTGCCTCAATGGGACCGTGCACCTCTC

CTGCCAGGAGAAACAGAACACCGTGTGCACCTGCCATGCAGGTTTCTTTC

TAAGAGAAAACGAGTGTGTCTCCTGTAGTAACTGTAAGAAAAGCCTGGAG

TGCACGAAGTTGTGCCTACCCCAGATTGAGAAT
```

SEQ ID NO: 3
30 kDa TNF Inhibitor

```
DSVCPQGKYI HPQNNSICCT KCHXGTYLYN DCPGPGQDTD

CRECESGSFT ASENHLRHCL SCSKCRKEMG QVEISSCTVD

RDTVCGCRKN QYRHYWSENL FQCFNCSLCL NGTVHLSCQE

KQNTVCTCHA GFFLRENECV SCSNCKKSLE CTKLCLPQIE N
```

SEQ ID NO: 4
MURINE CTLA-4

```
MACLGLRRYK AQLQLPSRTW PFVALLTLLF IPVFSEAIQV

TQPSVVLASS HGVASFPCEY SPSHNTDEVR VTVLRQTNDQ

MTEVCATTFT EKNTVGFLDY PFCSGTFNES RVNLTIQGLR

AVDTGLYLCK VELMYPPPYF VGMGNGTQIY VIDPEPCPDS

DFLLWILVAV SLGLFFYSFL VSAVSLSKML KKRSPLTTGV

YVKMPPTEPE CEKQFQPYFI PIN
```

SEQ ID NO: 5
mL63-9 Peptide-Fc Fusion

```
Met Gln Leu Gly Lys Leu Gln Cys Glu Leu Ser Thr Ala Gly Cys Pro

Asp Leu Pro Tyr Val Leu Glu Gly Gly Gly Gly Asp Lys Thr His

Thr Cys Pro Pro Cys Pro Ala Pro Glu Leu Leu Gly Gly Pro Ser Val

Phe Leu Phe Pro Pro Lys Pro Lys Asp Thr Leu Met Ile Ser Arg Thr

Pro Glu Val Thr Cys Val Val Val Asp Val Ser His Glu Asp Pro Glu

Val Lys Phe Asn Trp Tyr Val Asp Gly Val Glu Val His Asn Ala Lys

Thr Lys Pro Arg Glu Glu Gln Tyr Asn Ser Thr Tyr Arg Val Val Ser

Val Leu Thr Val Leu His Gln Asp Trp Leu Asn Gly Lys Glu Tyr Lys

Cys Lys Val Ser Asn Lys Ala Leu Pro Ala Pro Ile Glu Lys Thr Ile

Ser Lys Ala Lys Gly Gln Pro Arg Glu Pro Gln Val Tyr Thr Leu Pro

Pro Ser Arg Asp Glu Leu Thr Lys Asn Gln Val Ser Leu Thr Cys Leu

Val Lys Gly Phe Tyr Pro Ser Asp Ile Ala Val Glu Trp Glu Ser Asn

Gly Gln Pro Glu Asn Asn Tyr Lys Thr Thr Pro Pro Val Leu Asp Ser

Asp Gly Ser Phe Phe Leu Tyr Ser Lys Leu Thr Val Asp Lys Ser Arg

Trp Gln Gln Gly Asn Val Phe Ser Cys Ser Val Met His Glu Ala Leu

His Asn His Tyr Thr Gln Lys Ser Leu Ser Leu Ser Pro Gly Lys
```

SEQ ID NO: 6
mL6-17 Peptide-Fc Fusion

Met Asp Lys Thr His Thr Cys Pro Pro Cys Pro Ala Pro Glu Leu Leu

Gly Gly Pro Ser Val Phe Leu Phe Pro Pro Lys Pro Lys Asp Thr Leu

Met Ile Ser Arg Thr Pro Glu Val Thr Cys Val Val Val Asp Val Ser

His Glu Asp Pro Glu Val Lys Phe Asn Trp Tyr Val Asp Gly Val Glu

Val His Asn Ala Lys Thr Lys Pro Arg Glu Glu Gln Tyr Asn Ser Thr

Tyr Arg Val Val Ser Val Leu Thr Val Leu His Gln Asp Trp Leu Asn

Gly Lys Glu Tyr Lys Cys Lys Val Ser Asn Lys Ala Leu Pro Ala Pro

Ile Glu Lys Thr Ile Ser Lys Ala Lys Gly Gln Pro Arg Glu Pro Gln

Val Tyr Thr Leu Pro Pro Ser Arg Asp Glu Leu Thr Lys Asn Gln Val

Ser Leu Thr Cys Leu Val Lys Gly Phe Tyr Pro Ser Asp Ile Ala Val

Glu Trp Glu Ser Asn Gly Gln Pro Glu Asn Asn Tyr Lys Thr Thr Pro

Pro Val Leu Asp Ser Asp Gly Ser Phe Phe Leu Tyr Ser Lys Leu Thr

Val Asp Lys Ser Arg Trp Gln Gln Gly Asn Val Phe Ser Cys Ser Val

Met His Glu Ala Leu His Asn His Tyr Thr Gln Lys Ser Leu Ser Leu

Ser Pro Gly Lys Gly Gly Gly Gly Gly Ala Gln Met Ile Asp Trp Leu

Ser Gln Asn Arg Leu Phe Glu Gln Tyr Phe Glu Leu Ile Pro Pro Gly

Val Leu Glu

All references cited in the present disclosure are incorporated by reference in their entirety as if fully set forth herein.
The present invention and the manner in which it may be practiced are further illustrated by the following examples.

EXAMPLE 1

Expression and Purification of mL6-17 and mL63-9 Peptides as Fc-Fusion Proteins pAMG21 and pAMG21 Fc N-terminal and Fc C-terminal vectors: Expression plasmid pAMG21 (ATCC No. 98113) is derived from expression vector pCFM1656 (ATCC No. 69576) and the expression vector system described in U.S. Pat. No. 4,710,473, by following the procedure described in published International Patent Application WO 00/24782 (see the portion of Example 2 therein extending from pages 100-103, as well as FIGS. 17A and 17B). DNA sequences encoding an Fc domain were inserted into pAMG21 between the NdeI and BamHI restriction sites to generate plasmids that allowed fusion of the Fc domain either at the N-terminus or the C-terminus of a peptide.

GM221 (#2596): Host strain #2596, used for expressing Fc-peptide fusion proteins, is an *E. coli* K-12 strain modified to contain both the temperature sensitive lambda repressor c1857s7 in the early ebg region and the lacIQ repressor in the late ebg region. The presence of these two repressor genes allows the use of this host with a variety of expression systems, but the repressors are irrelevant to expression from luxPR. Details regarding its construction are found in WO 00/24782 (see Example 2 therein).

Construction of Fc-fusion polypeptides: Fc fusions to the mL6-17 and mL63-9 peptides were generated by cloning DNA fragments encoding the peptides into Fc N-terminal or C-terminal vectors as described below.

For fusion of the mL6-17 peptide to the N-terminus of Fc, constructs were made by annealing pairs of oligonucleotides ("oligos") to generate a duplex encoding the mL6-17 peptide and a linker comprising five glycine residues, one leucine residue and one glutamic acid residue as an NdeI to XhoI fragment. These duplex molecules were ligated into pAMG2'-Fc N-terminal vector which was also digested with NdeI and XhoI. The resulting ligation mixtures were transformed by electroporation into *E. coli* strain 2596 cells (GM221). Clones were screened for the ability to produce the recombinant protein product and to possess the gene fusion having a correct nucleotide sequence.

For fusion of the mL69.3 peptide to the C-terminus of Fc, constructs were made by annealing pairs of oligonucleotides ("oligos") to generate a duplex encoding five glycine residues, one alanine and one glutamic residue, the mL69.3 peptide, followed by one leucine residue and one glutamic acid residue as an ApaLI to XhoI fragment. These duplex molecules were ligated into the pAMG21-Fc C-terminal vector which was also digested with ApaLI and XhoI. The resulting ligation mixtures were transformed and screened as described above.

Expression in *E. coli*: Cultures of mL6-17 and mL63-9 Fc fusion constructs in *E. coli* GM221 were grown at 37° C. in Terrific Broth medium (See Tartof and Hobbs, "Improved media for growing plasmid and cosmid clones", Bethesda Research Labs Focus, Volume 9, page 12, 1987, cited in aforementioned Sambrook et al. reference). Induction of gene product expression from the luxPR promoter was achieved following the addition of the synthetic autoinducer, N-(3-oxohexanoyl)-DL-homoserine lactone, to the culture medium to a final concentration of 20 nanograms per milliliter (ng/ml). Cultures were incubated at 37° C. for an additional six hours. The bacterial cultures were then examined by microscopy for the presence of inclusion bodies and collected by centrifugation. Refractile inclusion bodies were observed in induced cultures, indicating that the Fc-fusions were most likely produced in the insoluble fraction in *E. coli*. Cell pellets were lysed directly by resuspension in Laemmli sample buffer containing 10% b-mercaptoethanol and then analyzed by SDS-PAGE. In each case, an intense coomassie-stained band of the appropriate molecular weight was observed on an SDS-PAGE gel.

Purification: Cells were broken in water (1/10) using high pressure homogenization (two passes at 14,000 PSI), and inclusion bodies were harvested by centrifugation (4000 RPM in a J-6B centrifuge for one hour). Inclusion bodies were solubilized in 6 M guanidine, 50 mM Tris, 10 mM DTT, pH 8.5, for one hour at a 1/10 ratio. For linear peptides fused to Fc, the solubilized mixture was diluted twenty-five times into 2 M urea, 50 mM Tris, 160 mM arginine, 2 mM cysteine, pH 8.5. The oxidation was allowed to proceed for two days at 4° C., allowing formation of the disulfide-linked compound (i.e., Fc-peptide homodimer). For cyclic peptides fused to Fc, this same protocol was followed with the addition of the following three folding conditions: (1) 2 M urea, 50 mM Tris, 160 mM arginine, 4 mM cysteine, 1 mM cystamine, pH 8.5; (2) 4 M urea, 20% glycerol, 50 mM Tris, 160mM arginine, 2 mM cysteine, pH 8.5; and (3) 4 M urea, 20% glycerol, 50mM Tris, 160 mM arginine, 4 mM cysteine, 1 mM cystamine, pH 8.5. The refolded protein was dialyzed against 1.5 M urea, 50mM NaCl, 50mM Tris, pH 9.0. The pH of this mixture was lowered to pH 5 with acetic acid. The precipitate was removed by centrifugation, and the supernatant was adjusted to a pH of from 5 to 6.5, depending on the isoelectric point of each fusion product. The protein was filtered and loaded at 4° C. onto an SP-Sepharose HP column equilibrated in 20 mM NaAc, 50 mM NaCl at the pH determined for each construct. The protein was eluted using a 20-colunm volume linear gradient in the same buffer ranging from 50 mM NaCl to 500mM NaCl. The peak was pooled and filtered. TNFbp was produced and purified as shown in EP 0 422 339, WO 92/16221and WO 95/34326. Ovalbumin was obtained from Sigma (St. Louis, MO).

EP 0 422 339 states at pages 18 and 19: "C. Purification of the 30kDa TNF Inhibitor Twenty liters of urine from a patient diagnosed with renal dysfunction was concentrated to 200 ml with an Amicon YM5 membrane. The concentrate was then dialyzed at 4° C. against 0.0251 Tris-Cl, pH 7.5, and subsequently centrifuged in a JA14 rotor at 10,000 rpm for 30 minutes. The supernatant was then loaded onto a 40×4.5 cm DEAE Sepharose CL-6B column equilibrated with 0.0251 Tris-Cl, pH 7.5 and extensively rinsed with equilibration buffer until the $OD_{280}$ of the effluent returned to baseline. Chromatography was accomplished using a linear gradient from 0-0.05 M sodium chloride in 0.025 M Tris-Cl pH 7.5 and monitored by $OD_{280}$. Column fractions were collected, and assayed for TNF inhibitor activity using the native gel assay. The TNF inhibitor eluted elutes in a rather sharp peak at 80mM NaCl. FIG. 6A shows the $OD_{280}$ profile of the DEAE Sepharose CL-6B chromatography of 20 l urine. FIG. 6B shows the autoradiograph of the corresponding native gel assay indicating a peak of the TNF inhibitor at fractions 57-63, which is about 80mM NaCl.

The TNF inhibitor was further purified using a TNF affinity column. Recombinant TNF was expressed in BL21/DE3 at about 10-20% total cell protein. The cell pellet was French-pressed at 20,000 psi and the soluble material dialyzed at 4° C. against 0.025 M Tris-Cl pH 8.0. The dialyzed lysate was 0.2 micron-filtered and loaded onto a Mono-Q FPLC column equilibrated with 0.025M Tris-Cl ph 8.0. A linear gradient from 0 to 0.5 M NaCl in 0.025 M Tris-Cl pH 8.0 was run and monitored by $OD_{280}$. One ml fractions were collected and analyzed for purity by SDS-PAGE. The subsequent TNFa pool was about 95% pure based on Coomassie-stained SDS-PAGE and was fully active based on a Bradford protein assay, using lysozyme as a standard, and an ME 180 bioassay, using Amgen's TNFa as a standard (Bradford, M. Annal. Biochem. 72, 248-254 (1976)). TNFa was concentrated in an Amicon Centriprep-10 to about 25 mg/ml, dialyzed against 100 mM $NaHCO_3$, pH 8.5, and coupled to Affigel-15 resin at 25 mg TNF/ml resin. A coupling efficiency of greater than 80% yielded a high capacity resin which was used to further purify the TNF inhibitor. PMSF, at a final concentration of 1-4 mM, was added to the DEAE CL-6B pool and applied to a 4×1cm TNF affinity colunm equilibrated at 4° C. with 0.025 M Tris-Cl pH 7.5 at a flow rate of 0.1 ml/min. The column was then rinsed with 0.025 M Tris-Cl pH 7.5 until the $OD_{280}$ of the effluent returned to baseline. The column was subsequently eluted with 0.05 M NaPhos pH 2.5 and monitored by $OD_{280}$. FIG. 7 shown the $OD_{280}$ profile of the 0.05 M NaPhos pH 2.5 elution from the TNF affinity column. The TNF inhibitor was purified to homogeneity by reverse phase HPLC on a Syn-cropak RP-8 (C8) colunm. The $OD_{280}$ peak from the TNF affinity colunm was pooled and immediately loaded onto a RP-8 column, equilibrated with 0.1 % $TFA/H_2O$, a linear 1%/min gradient of 0.1% TFA/acetonitrile was run, from 0-50% and monitored by $OD_{215}$ and $OD_{280}$. Fractions were collected and assayed from bioactivity using L929 cells and the native gel assay described in Example 1B. Both of these assays indicate bioactivity at fractions 28-32 which corresponds to a peak of $OD_{215}$ and $OD_{280}$ eluting at 18% acetonitrile. FIGS. 8A and 8B show the chromatographic profile of the TNF affinity pool on a Syncropak RP-8 colunm with the corresponding bioactivity from the L929 cytotoxicity assay. FIG. 8B shows a silver stained 15% reducing SDS-PAGE of the RP-8 pool indicating a single band at 30kDa."

EP 0 422 339 states at page 27: "Example 14. Isolation of 40kDa TNF inhibitor cDNA sequences from PMNPHA-induced U937 cells. U937 mRNA was isolated from cells that had been induced by PMA/PHA for 9 hours. It was then selected on an oligo-dT colunm, and the polyadenylated mRNA thus isolated was used to make dscDNA using reverse transcriptase followed by *E. coli* polymerase I/RNase H. The dscDNA was subjected to a polymerase chain reaction using, as primers, the degenerate probes (40KD-P1' and 40KD-P7) shown in Table 5. The DNA products from this reaction were probed on a Southern blot with probe 40KD-P6'(see Table 5) identifying a single band that contained this sequence. This band was isolated on an agarose gel and cloned into MI3 phage DNA (strain mp 18). After transformation into *E. coli* strain JM109 and plating on medium containing X-gal and IPTG, clear plaques were identified that contained the correct cDNA insert. The sequence of the DNA in this clone is shown in FIG. 37 along with the translation product predicted from this sequence. This amino acid sequence matches the peptide sequence shown in FIG. 36 (residues 12-104) and FIG. 38."

WO95/34326 states at pages 8-9:"One TNF binding protein ("TNFbp") is the extracellular portion of the p55 TNF receptor or the TNF receptor I. In vivo, the extracellular portion of the receptor is shed and circulates in the bloodstream as a 30kDa glycosylated protein which binds to TNF. This binding protein is also referred to TNFbp-I or the 30kD TNFbp. The purification and amino acid and nucleic acid sequences of this TNF binding protein are set forth in published European Patent Application No. 90 113 673.9, which is incorporated herein by reference. This published reference also teaches the recombinant production of glycosylated and deglycosylated forms of this TNF inhibitor. Although the actual molecular weight of the deglycosylated form of this inhibitor is approximately 18kDa, the term "30kDa TNF inhibitor" includes the glycosylated and deglycosylated forms. As used herein, the terms "naturally-occurring," "native," and "wild-type" are synonymous. European Patent Application No. 90 113 673.9, incorporated herein by reference, also sets forth the purification and amino acid and nucleic acid sequences of another TNF inhibitor, called the 40kDa TNF inhibitor. Also called TNFbp-II, this inhibitor, in its naturally-occurring form, is the glycosylated extracellular portion of the p75 or p85 TNF receptor. European Patent Application No. 90 112 673.9 also teaches the recombinant production of the glycosylated and deglycosylated forms of this "40kDa" inhibitor. The nucleic and amino acid sequences of the native 40kDa TNF inhibitor are set forth in this published reference. Although the molecular weight of the deglycosylated form is not 40kDa, both the glycosylated and deglycosylated forms of this TNFbp are referred to as "40kDa TNF inhibitor." European Patent Application No. 90 112 673.9, incorporated herein by reference, further teaches the recombinant production of two TNF inhibitors which are portions of the full length "40kDa" binding protein. These two truncates are called the "Δ51" and "Δ53" TNF inhibitors. The amino acid and nucleic acid sequences of the Δ51 and Δ53 inhibitors are set forth in this published reference.

Murine CTLA-4-Fc used herein was a fusion of an Fc domain to the carboxy terminus of the extracellular domain of murine CTLA-4. The full-length sequence of murine CTLA-4 is shown in SEQ ID NO: 4. Conditioned medium (CM) from CHO cells, which were expressing the extracellular domain of murine CTLA-4 fused to human IgG1 Fc, was concentrated 15-fold using a Pellicon ultrafiltration device fitted with a 50 kD MWCO screen channel cassette (Millipore, New Bedford, Mass.). The concentrated CM was filtered through 0.22 μm then batch bound to recombinant Protein A sepharose resin (Amersham Pharmacia, Uppsala, Sweden), overnight at 4° C. After binding, the resin was packed into a glass column and washed with several column volumes of PBS before eluting with ImmunoPure IgG elution buffer (Pierce, Rockford Ill.). The elution was neutralized by adding 5% v/v 1M Tris HCl, pH 9.2 then dialyzed vs. two 20-fold volumes of PBS at 4° C. for at least 8 hours for each dialysis.

EXAMPLE 2

CTLA-4Fc Decreases the Incidence of Immune Responses to Immunogenic Therapeutic Compositions Ten male B10.RIII mice of three to four months old were administered an immunogenic therapeutic protein (mL6-17 peptide-Fc fusion, mL63-9 peptide-Fc fusion, or TNFbp) or a control (ovalbumin) alone or in combination with a conspecific CTLA construct (mCTLA-4Fc). Administration occurred over a ten day dosing cycle, e.g., dosing on days 0, +1, +2, +4, +6, +8, +10, by intraperitoneal injection (i.p.). Immunogenic therapeutic compositions and control were administered at 4 mg/kg, either alone or with 2 mg/kg mCTLA-4Fc. All proteins were diluted in PBS.

Mice injected with OVA, ML6-17 and TNFbp, and m63.9 alone generally developed antibodies by day 24. In contrast, no or markedly reduced antibody titers were found to the otherwise immunogenic therapeutic compositions in mice injected with both the immunogenic therapeutic composition and CTLA-4 (data not shown).

EXAMPLE 3

CTLA-4Fc Also Greatly Increases the Probability that Tolerance will be Induced to a Co-administered Immunogenic Therapeutic Composition The mice of Example 2 were subsequently challenged on days +30, +31, +32, +34, +36, +38, and +40 with 4 mg/kg of the same previously administered immunogenic composition alone. Serum samples were collected on days 24, 54 and 68 and assayed by BIAcore for protein-specific antibody responses against the immunogenic compositions, which were then compared to day −2 day (pre-study bleed) base values.

Biosensor analysis was performed with a BIAcore 3000 instrument. TNFbp, Ovalbumin, ML6-17, and m63.9 were immobilized by amine chemistry directly to a CM 5 sensor chip in separate flow cells. Each mouse serum sample was diluted 1:10 with Hepes Buffered Saline containing Carboxymethyl-dextran and Polysorbant 20. The diluted samples were injected over the surface of the sensor chip for detection of specific antibodies to their respective immobilized drug. The amount of binding was monitored in real time and expressed in response units (RU). Each biosensor immunoassay run included serum samples (pre-dose and post-dose), negative control (10% pooled mouse serum diluted in sample diluent), and positive control (anti-drug antibody in 10% pooled mouse diluted in sample diluent).

As can be seen in FIG. 1, the percent incidence of positive antibody responses to a subsequent challenge is unexpectedly significantly decreased when one compares groups of mice that were previously administered an immunogenic therapeutic composition alone or in combination with CTLA-4Fc. The results show that co-administration of CTLA-4Fc induces tolerance, even for strongly immunogenic therapeutic proteins like TNFbp, for a significant period of time.

EXAMPLE 4

Optimization of CTLA-4 Administration Regimen for Induction of Tolerance

Five groups of male B10.RIII mice were injected i.p. 7 times over a ten day period with TNFbp (4 mg/kg) as in Example 2, while each group was administered a different regimen of 2 mg/kg mCTLA-4Fc, as follows: Group 1 (7+7)—mCTLA-4Fc administrated on days 0, +1, +2, +4, +6, +8, +10; Group 2 (7+5)—mCTLA-4Fc administrated on days 0, +1, +2, +4, +6; Group 3 (7+4)—mCTLA-4Fc administrated on days 0, +1, +2, +4; Group 4 (7+3)—mCTLA-4Fc administrated on days 0, +1, +2; and Group 5 (7+0)—no CTLA-4Fc administrated (control).

Figure 2:
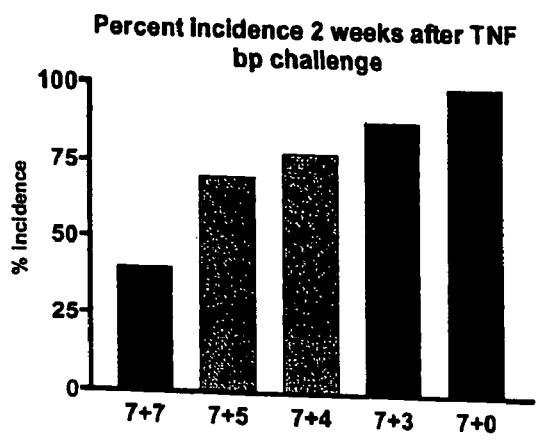
FIG. 2A shows a graphical comparison of the percent incidence of an antibody response 2 weeks post challenge (Day 54) between groups of mice administered different regimens of CTLA-4.
FIG. 2B shows that the mean response unit (RU) value is suppressed with all CTLA-4Fc regimen groups compared to no treatment. Similar results were seen at 4 weeks after challenge (day 68) as shown in FIGS. 2C and 2D.
Figure 2:
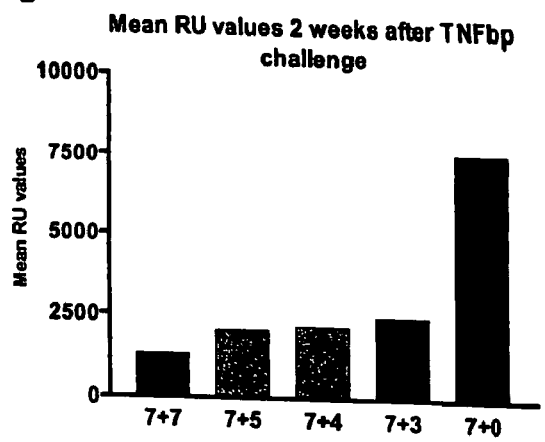
Figure 2:
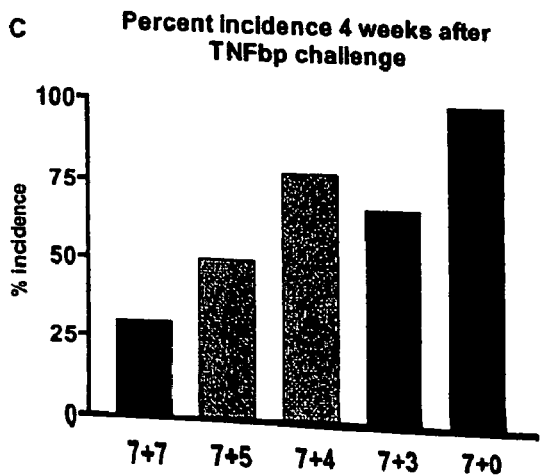
Figure 2:
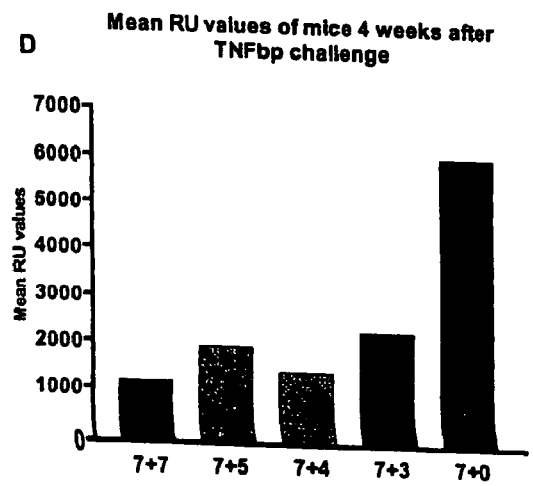

Thus, group 1 received 7 doses of immunogenic protein and 7 doses of mCTLA-4Fc (7+7). Group 2 received 7 doses of immunogenic protein and 5 doses of mCTLA-4Fc (7+5). Group 3 received 7 doses of immunogenic protein and 4 doses of mCTLA-4Fc (7+4). Group 4 received 7 doses of immunogenic protein and 3 doses of mCTLA-4Fc (7+3). And group 5 received 7 doses of immunogenic protein and no doses of mCTLA-4Fc (7+0). As in Example 3, mice were challenged from days 30-40 with 7 doses of TNFbp and bled on days 54 and 68. The results of the experiment are shown in FIGS. 2 A-D. Antibody responses were compared to pre-study bleed values.

FIG. 2A shows a graphical comparison of the percent incidence of an antibody response 2 weeks post challenge (Day 54) between groups of mice administered different regimens of CTLA-4. FIG. 2B shows that the mean RU value is suppressed with all CTLA-4Fc regimen groups compared to no treatment. Unexpectedly, antibody levels were much less dependent on treatment regimen than the percentage incidence of antibody positive mice. Similar results were seen at 4 weeks after challenge (day 68) as shown in FIGS. 2C and 2D. Incidence was around 25% for the 7+7 group and had much suppressed antibody levels as compared to the control.

EXAMPLE 5

Longevity of Immune Tolerance

To test the longevity of immune tolerance caused by co-administration of an immunogenic therapeutic composition and CTLA-4Fc, male B10III mice (n=10) were injected i.p as in Example 2 on day 0, +1, +2, +4, +6, +8, +10 with both TNFbp and mCTLA-4Fc at 4mg/kg and 2mg/kg respectively. Mice were then challenged on days 60-70 with TNFbp using the 7 injection protocol described supra. Mice were then bled on day 84 and 96 and assayed for antibody responses to TNFbp. The results of the experiment are shown in FIG. 3.

Figure 3:
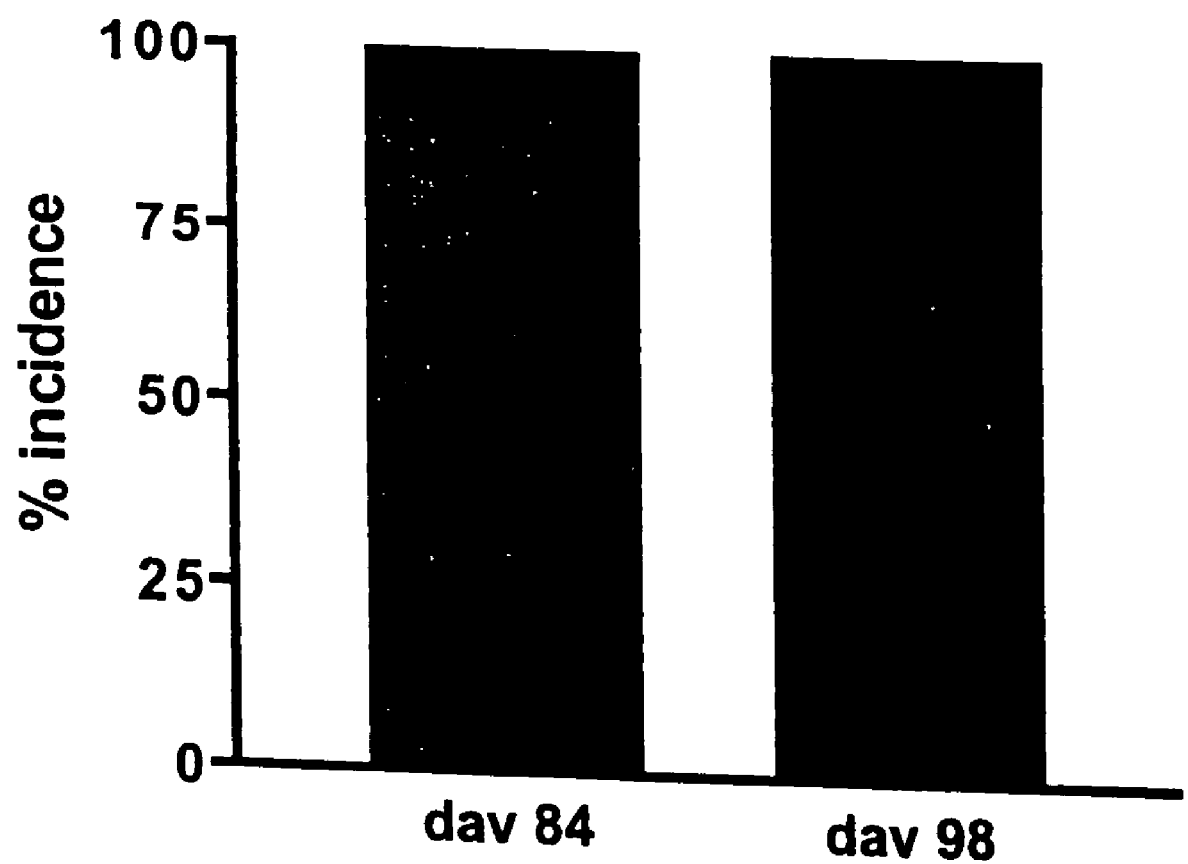
FIG. 3 shows the percent incidence of anti-TNFbp antibody response on day 84 and 98 (14 and 28 days after days 60-70 challenge) in animals tolerized with mCTLA-4Fc from day 0-10.

In contrast to the mice of Example 3 (data shown in FIG. 1), animals challenged after day 60 developed antibodies to the immunogenic therapeutic composition (FIG. 3). These data suggest that immune tolerance is developed for a finite amount of time. In this example, under the regimen of the experiment, immune tolerance is less than 60 days for TNFbp in mice.

EXAMPLE 6 Immune Tolerance is Specific to the Therapeutic Immunogen and Not Merely a General Immune Suppression.

The same strains of mice were injected (7+7) on days 0-10 as before. That is with 7 injections of TNFbp along with 7 injections i.p. of mCTLA-4Fc. This time on day 30-40, animals (n=10) were injected with OVA protein (4 mg/kg) or TNFbp (4 mg/kg). Mice were then bled on days 54 and assayed for antibody-specific responses to the immunogenic protein.

Figure 4:
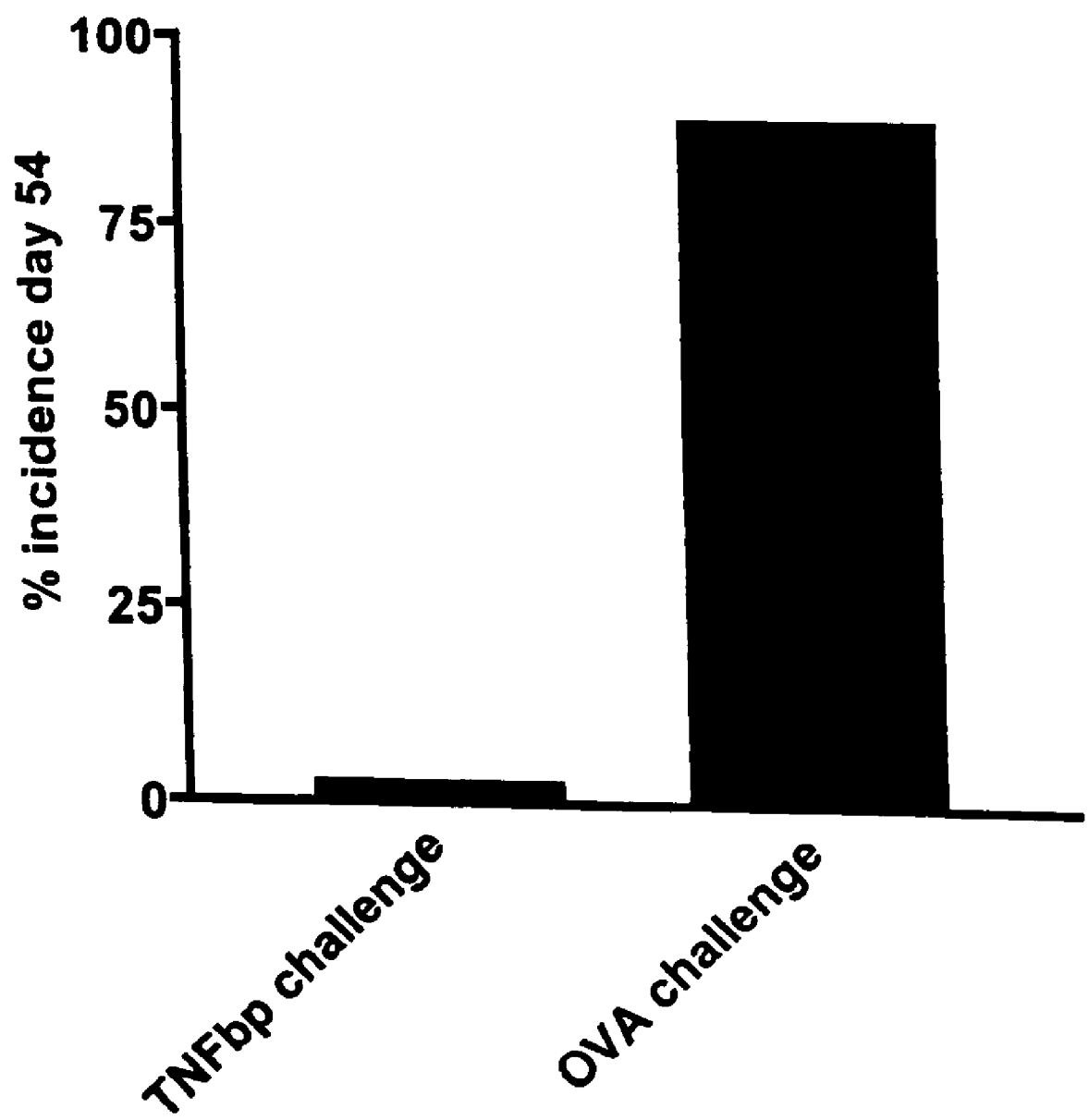
FIG. 4 shows that CTLA-4 administration with an immunogenic therapeutic molecule tolerizes a responses to the immunogenic therapeutic molecule but not to a naive antigen, e.g., antigen specific tolerance, not general immune suppression, is the result of CTLA-4 administration.

As shown in FIG. 4, mCTLAFc completely tolerized responses to TNFbp but not to a naive antigen. Day 68 responses were almost identical. The data suggest that T-cells can be made tolerant to an immunogenic therapeutic composition when it is co-administered with CTLA-4.

Given that TNFbp is a highly immunogenic therapeutic molecule, see, e.g., Moreland, et al., The Journal of Rheumatology 27:601-609, we have surprisingly found, inter alia, that CTLA-4, when administered in an effective time interval relative to the administration of TNFbp, induces tolerance to and markedly decreases the immunogenicity of TNFbp in a specific manner.

Although the invention has been described with reference to certain embodiments thereof, it will be appreciated by those skilled in the art that modifications and variations may be made without departing from the spirit and scope of the invention as defined in the appended claims.

The invention claimed is:

1. A method of treating an immune reaction to an immunogenic therapeutic protein selected from the group consisting of a 30kDa TNF inhibitor, a 40kDa TNF inhibitor, and a peptide-Fc fusion molecule which binds to nerve growth factor, comprising administering a therapeutically effective amount of CTLA-4 comprising a polypeptide, selected from the group consisting of (a) SEQ ID NO: 1, (b) extracellular domain of CTLA-4, (c) residues 1-124 of SEQ ID NO:1, and (d) a variant of any of the CTLA-4 peptides (a)-(c) having a substitution of a different amino acid for $Ser^{25}$, $Ala^{29}$, $Thr^{30}$, $Leu^{104}$ and/or $Gly^{105}$ relative to SEQ ID NO:1, to a subject before, during, and/or after administration of the immunogenic therapeutic protein, wherein administration of CTLA-4 decreases the incidence or intensity of an immune reaction caused by the immunogenic therapeutic protein in the subject.

2. The method of claim 1 wherein CTLA-4 is linked to an immunoglobulin heavy chain constant region.

3. The method of claim 1 wherein the therapeutic protein is a recombinant protein and is fully human.

4. The method of claim 1 wherein the therapeutic protein is recombinant and at least a portion of the therapeutic protein comprises a non-human component.

5. The method of claim 1 wherein the therapeutic protein is a TNFbp of SEQ ID NO:3.

6. The method of claim 1 wherein the therapeutic protein is a peptide-Fc fusion molecule which binds nerve growth factor, the peptide-Fc fusion molecule selected from the group consisting of SEQ ID NO:5 and SEQ ID NO:6.

7. The method of claim 1 wherein the effective amount of CTLA-4 is from about 0.1 mg/kg to about 100 mg/kg of the body weight of the subject.

8. A method of tolerizing a subject to an immunogenic therapeutic protein selected from the group consisting of a 30kDa TNF inhibitor, a 40kDa TNF inhibitor, and a peptide-Fc fusion molecule which binds to nerve growth factor, comprising administering a therapeutically effective amount of CTLA-4, comprising a polypeptide, selected from the group consisting of (a) SEQ ID NO: 1, (b) extracellular domain of CTLA-4, (c) residues 1-124 of SEQ ID NO:1, and (d) a variant of any of the CTLA-4 peptides (a)-(c) having a substitution of a different amino acid for $Ser^{25}$, $Ala^{29}$, $Thr^{30}$, $Leu^{104}$ and/or $Gly^{105}$ relative to SEQ ID NO:1, to a subject before, during, and/or after administration of the immunogenic therapeutic protein, wherein administration of CTLA-4 decreases the incidence or intensity of an immune reaction caused by the immunogenic therapeutic protein in the subject.

9. The method of claim 8 wherein CTLA-4 is linked to an immunoglobulin heavy chain constant region.

10. The method of claim 8 wherein the therapeutic protein is a recombinant protein and is fully human.

11. The method of claim 8 wherein the therapeutic protein is recombinant and at least a portion of the therapeutic protein comprises a non-human component.

12. The method of claim 8 wherein the therapeutic protein is a TNFbp of SEQ ID NO: 3.

13. The method of claim 8 wherein the therapeutic protein is a peptide-Fc fusion molecule which binds nerve growth factor, the peptide-Fc fusion molecule selected from the group consisting of SEQ ID NO:5 and SEQ ID NO:6.

14. The method of claim 8 wherein the effective amount of CTLA-4 is from about 0.1 mg/kg to about 100 mg/kg of the body weight of the subject.

15. The method of claim 8 wherein the administration of the therapeutic protein is continued after the subject has been tolerized to the therapeutic protein.

16. A method of decreasing an antibody titer of an immune response in a subject receiving an immunogenic therapeutic protein selected from the group consisting of a 30kDa TNF inhibitor, a 40kDa TNF inhibitor, and a peptide-Fc fusion molecule which binds to nerve growth factor, comprising administering a therapeutically effective amount of CTLA-4, comprising a polypeptide, selected from the group consisting of(a) SEQ ID NO: 1, (b) extracellular domain of CTLA-4, (c) residues 1-124 of SEQ ID NO:1, and (d) a variant of any of the CTLA-4 peptides (a)-(c) having a substitution of a different amino acid for $Ser^{25}$, $Ala^{29}$, $Thr^{30}$, $Leu^{104}$ and/or $Gly^{105}$ relative to SEQ ID NO:1, to a subject before, during, and/or after administration of the immunogenic therapeutic protein, wherein administration of CTLA-4 decreases the incidence or intensity of an immune reaction caused by the immunogenic therapeutic protein in the subject.

17. The method of claim 16 wherein CTLA-4 is linked to an immunoglobulin heavy chain constant region.

18. The method of claim 16 wherein the therapeutic protein is a recombinant protein and is fully human.

19. The method of claim 16 wherein the therapeutic protein is recombinant and at least a portion of the therapeutic protein comprises a non-human component.

20. The method of claim 16 wherein the therapeutic protein is a TNFbp of SEQ ID NO:3.

21. The method of claim 18 wherein the therapeutic protein is a peptide-Fc fusion molecule which binds nerve growth factor, the peptide-Fc fusion molecule selected from the group consisting of SEQ ID NO:5 and SEQ ID NO:6.

* * * * *

UNITED STATES PATENT AND TRADEMARK OFFICE
CERTIFICATE OF CORRECTION

PATENT NO. : 7,579,316 B2
APPLICATION NO. : 11/057923
DATED : August 25, 2009
INVENTOR(S) : Khare et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 416 days.

Signed and Sealed this

Fourteenth Day of September, 2010

David J. Kappos
*Director of the United States Patent and Trademark Office*